United States Patent
Bernhardt

(10) Patent No.: US 7,811,520 B2
(45) Date of Patent: Oct. 12, 2010

(54) INTEGRATED PARAFOIL THREAT AGENT SENSOR SYSTEM AND METHODS

(75) Inventor: Roger D. Bernhardt, O'Fallon, MO (US)

(73) Assignee: The Boeing Company, Chicago, IL (US)

( * ) Notice: Subject to any disclaimer, the term of this patent is extended or adjusted under 35 U.S.C. 154(b) by 401 days.

(21) Appl. No.: 12/039,919

(22) Filed: Feb. 29, 2008

(65) Prior Publication Data

US 2009/0220384 A1    Sep. 3, 2009

(51) Int. Cl.
*G01N 7/00*     (2006.01)
*G01N 21/00*    (2006.01)
*G01N 33/00*    (2006.01)
*G01N 1/22*     (2006.01)

(52) U.S. Cl. .............................. 422/83; 422/50; 422/55; 422/67; 422/93; 73/23.2; 73/31.01; 436/181

(58) Field of Classification Search ................... 422/83; 73/31.01

See application file for complete search history.

(56) References Cited

U.S. PATENT DOCUMENTS

| | | | |
|---|---|---|---|
| 6,066,295 A | 5/2000 | Bernstein et al. | |
| 6,700,484 B2 | 3/2004 | Bartholomew et al. | |
| 7,073,748 B2* | 7/2006 | Maurer et al. | 244/1 R |
| 7,283,156 B1* | 10/2007 | Morgan | 348/144 |
| 7,323,343 B2 | 1/2008 | Cox et al. | |
| 2001/0042843 A1 | 11/2001 | Cox et al. | |
| 2005/0211415 A1 | 9/2005 | Arts et al. | |
| 2007/0224087 A1* | 9/2007 | Ding | 422/83 |

* cited by examiner

*Primary Examiner*—Jill Warden
*Assistant Examiner*—Jennifer Wecker
(74) *Attorney, Agent, or Firm*—Armstrong Teasdale LLP

(57) ABSTRACT

A method for collecting and sensing a column of air in near real-time to detect one or more agents dispersed within the air column is described. The method includes passing the column of air through a port in a parafoil, the parafoil configured with a flow-through sensor suite located in the port and operable such that the column of air passes through the sensor suite, operating the sensor suite to test the column of air for the one or more agents, and receiving test results from the sensor suite.

20 Claims, 6 Drawing Sheets

INTEGRATED PARAFOIL THREAT AGENT SENSOR SYSTEM AND METHODS

BACKGROUND OF THE INVENTION

This invention relates generally to agent and contaminant detection and identification, and more specifically, to an integrated parafoil threat agent sensor system and the methods associated therewith.

While detection and identification of agents and contaminants in ground-based situations is a fairly mature science, detection and identification of airborne agents and contaminants is not as mature. Particularly, there have been no systems promulgated that solve the problem of collecting and detection of agents and contaminants in a column of air, in real time. More particularly, some of these agents/contaminants may have the potential to contain threatening or contaminating materials such as aerosol or particulate chemicals or biological agents or other contaminants. The detection and identification problem is especially challenging when persistent measurements across a large column of air are attempted. This is in part due to the transient and vaporous nature of aerosols and particulates in free space. Sensors to detect such agents have response time constraints, sensitivity to various interferences and concentration threshold sensitivities.

Previous efforts to sense, identify, and discriminate on a standoff basis have had a limitation in their overall effectiveness in one or both of size and range, false alarms, specificity, sensitivity and persistence. Such problems limit the effectiveness of free space discriminating and sensing of threat agents across the spectrum of their characteristic behaviors in free space.

BRIEF DESCRIPTION OF THE INVENTION

In one aspect, a method for collecting and sensing a column of air in near real-time to detect one or more agents dispersed within the air column is provided. The method includes passing the column of air through a port in a parafoil, the parafoil configured with a flow-through sensor suite located in the port and operable such that the column of air passes through the sensor suite, operating the sensor suite to test the column of air for the one or more agents, and receiving test results from the sensor suite.

In another aspect, a system for airborne detection of one or more agents dispersed within the atmosphere is provided. The system includes a parafoil operable to pass through a portion of the atmosphere, a sensor suite attached to the parafoil that is operable to determine if one or more agents are in the atmosphere portion, and a processing device configured to receive data from the sensor suite and utilize the received data to discriminate from multiple received signatures to establish the presence or absence of at least one specific agent type.

The features, functions, and advantages that have been discussed can be achieved independently in various embodiments of the present invention or may be combined in yet other embodiments further details of which can be seen with reference to the following description and drawings.

DETAILED DESCRIPTION OF THE INVENTION

Figure 1:
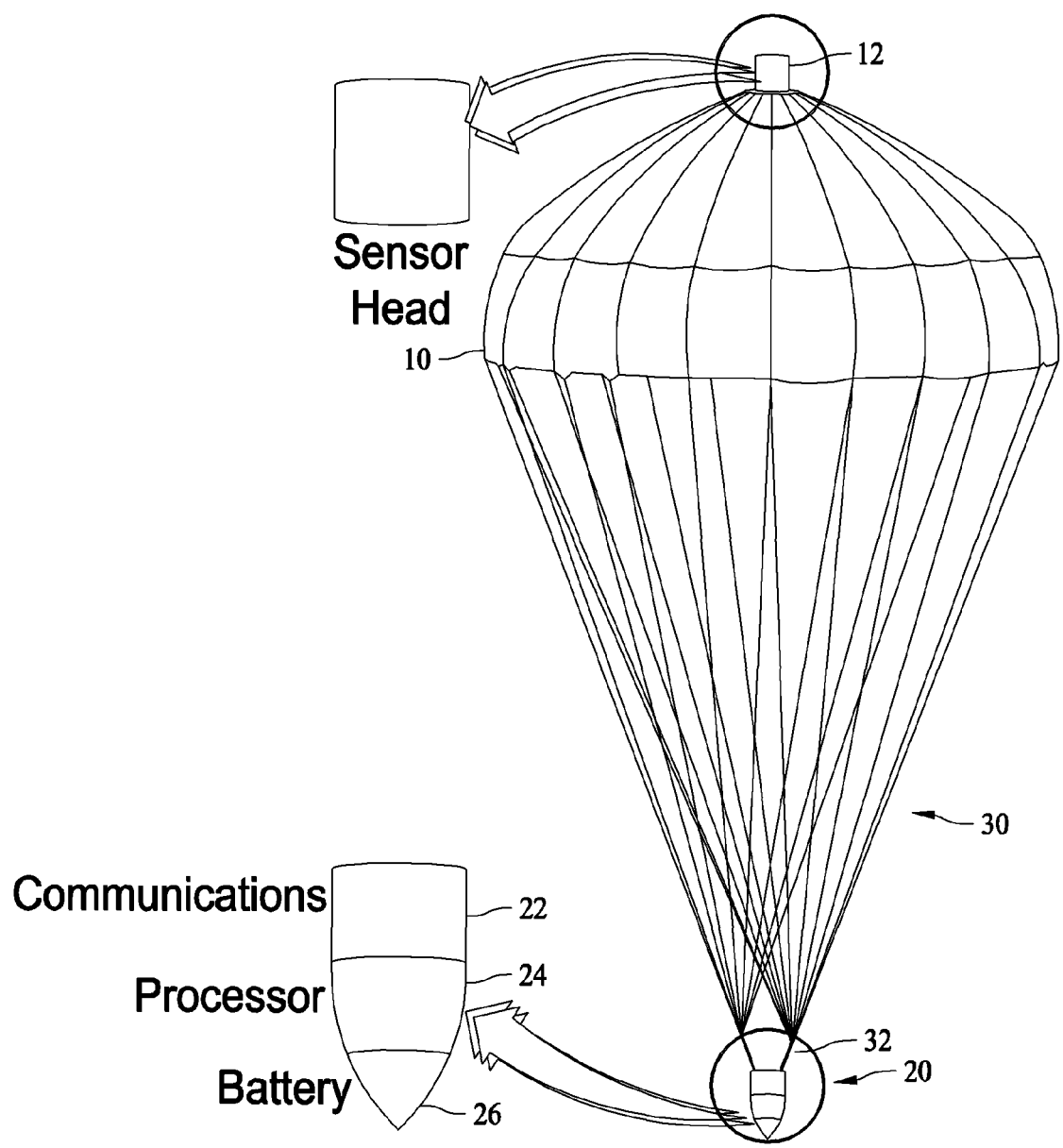
FIG. 1 is an illustration of a passive parafoil having a flow through center port, a sensor head mounted in the center port.

The embodiments described herein can be generally described as one or more sensors embedded in an expandable funnel whereby one or more sensing devices per sensor are deployed. Specifically, and referring now to FIG. 1, which illustrates a deployed parachute, or parafoil 10, which operates as an expandable funnel during deployment and subsequent utilization. While illustrated as a parachute, parafoil 10 in other embodiments, is configured as one of a square chute, a funnel shaped expandable collector, or any other device capable of funneling air to, and through, a sensing unit such as sensor head 12.

Parafoil 10 includes, at its center, a sensor head 12 which receives a directed airflow based on the operation of the parafoil 10. Communicatively coupled to sensor head 12, and utilized as the load for parafoil 10, is a processing module 20 that includes, at least in the embodiment illustrated, a communications module 22, a processor module 24, and a battery 26. As illustrated, the processing module 20 is suspended from lines 30 that extend from a perimeter of parafoil 10 to a harness 32 that connects the lines 30 to the processing module 20.

Figure 2:
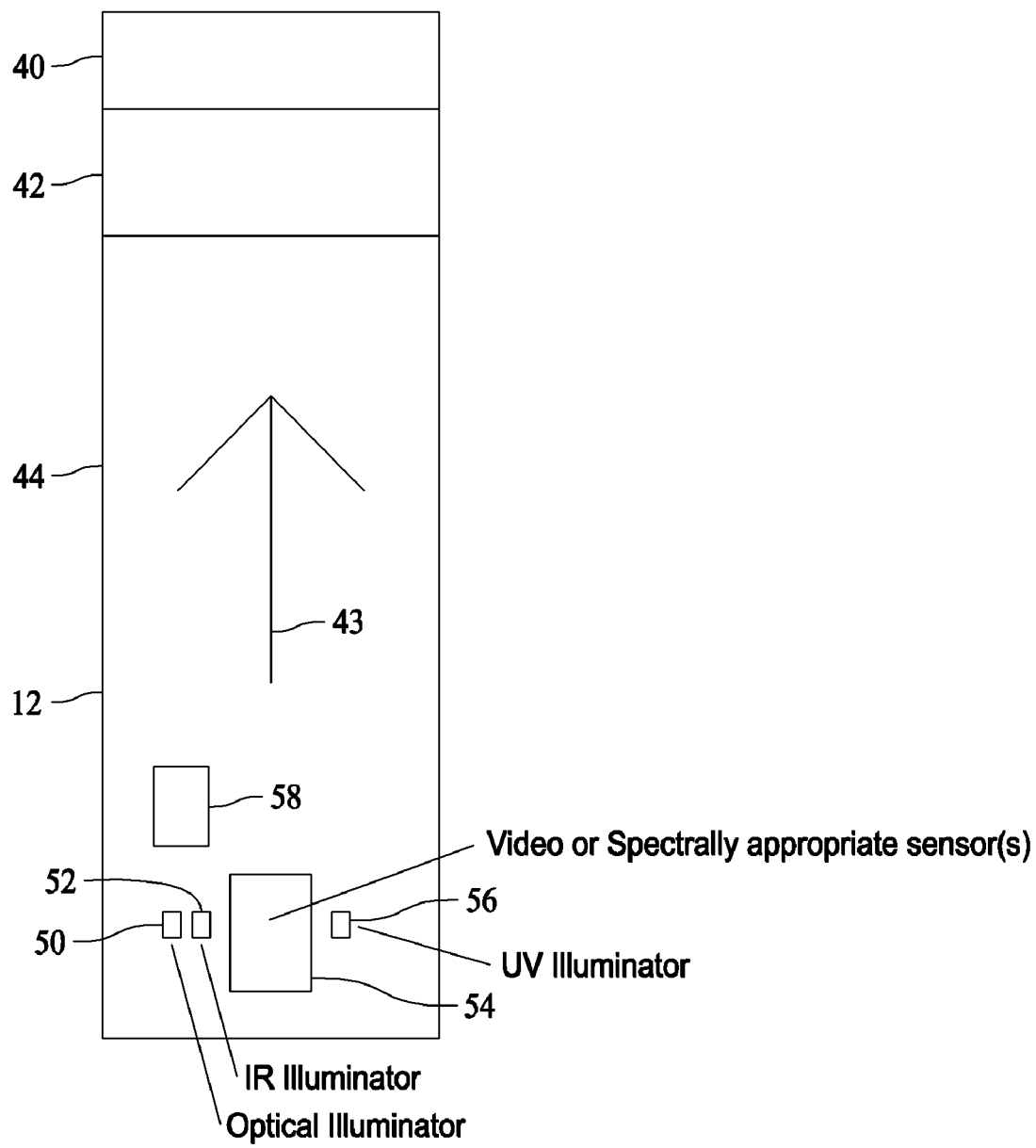
FIG. 2 is a schematic diagram of one embodiment of a sensor head

FIG. 2 is a schematic diagram of one embodiment of a sensor head 12. In the illustrated embodiment, sensor head 12 includes an optional fan 40 for pulling an airflow through the sensor head 12. Sensor head 12 further includes sensor targets 42, which in alternative embodiments includes a plurality of sensing elements and/or sensing taggants (not shown in FIG. 2) coated or embedded thereon. Liquid-based sensors may be hosted on porous substrates or otherwise configured for interaction with an air flow 43 through the sensor head 12. Sensors may be mounted on vanes (not shown in FIG. 2) within the sensor head 12 or may even be mounted on the blades or mounting structure associated with the fan 40. Signatures of the integrated suite of sensors are used to discriminate signals using a variety of sensor modalities, providing the capabilities described herein. The air flow path 43, in one embodiment is directional, as illustrated by the arrow in FIG. 2. In other embodiments, the airflow path 43 incorporates an open air configuration, with illumination and sensing elements disbursed within the sensor head 12.

As further described below, to determine a composition of particles passing along the air flow path 43, the sensor head 12 may incorporate one or more of an optical illuminator 50, an infrared illuminator 52, a video or other spectrally appropriate sensor 54, an ultraviolet illuminator 56, or other sensors 58 as appropriate. As particles pass through the air flow path 43, they are illuminated by one or more of the various illuminators described above and the sensors are utilized to determine particulate composition based on the reaction of the particles to illumination.

Figure 3:
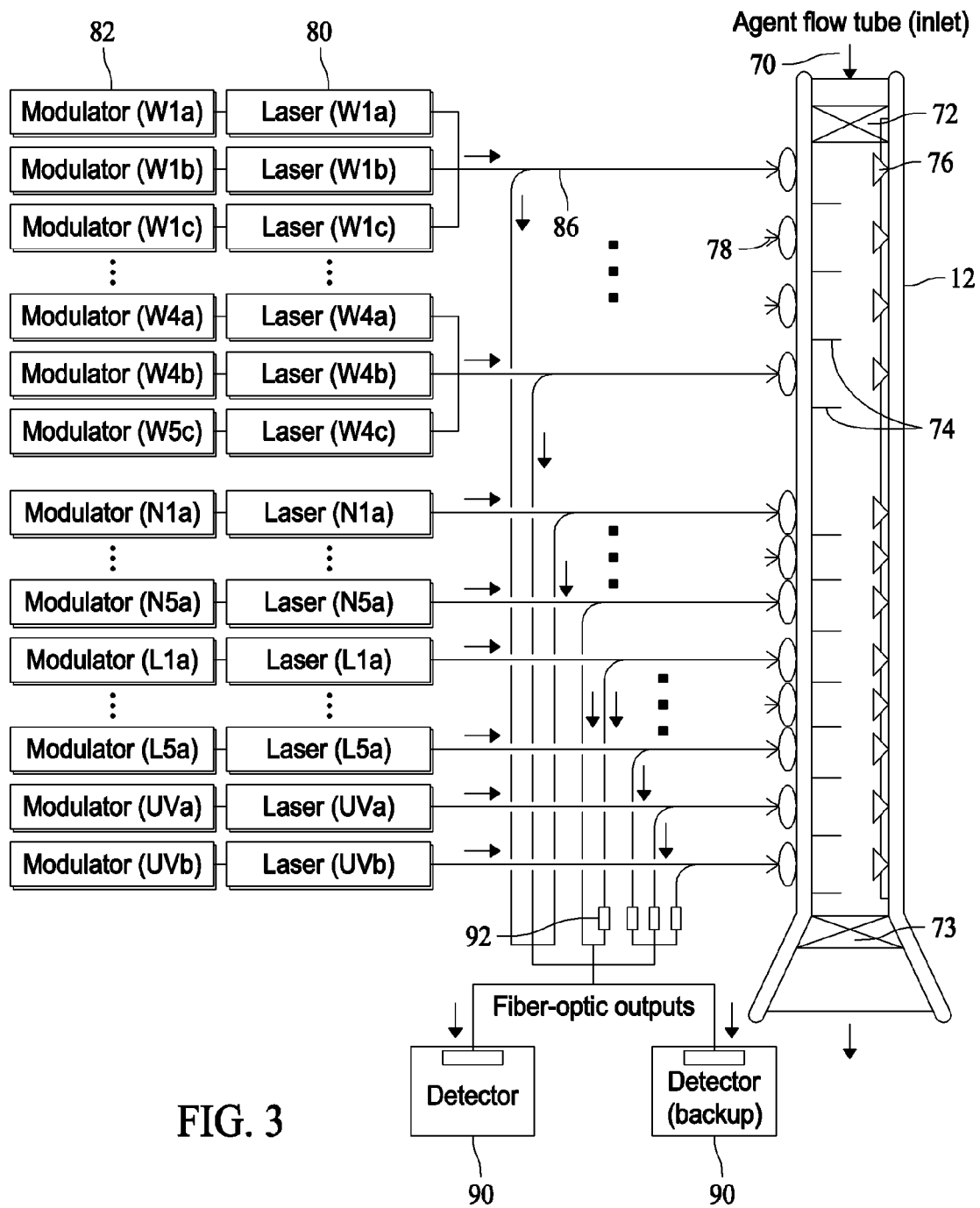
FIG. 3 is a detailed schematic diagram of a portion of a sensor head.

FIG. 3 is a detailed schematic diagram of one portion of the sensor head 12, further illustrating illumination and spectral sensing. In the illustrated embodiment, sensor head 12 includes a flow-through threat agent and/or contaminant sensor suite embedded in or on a flow collector. The sensor head 12 includes an air inlet 70 where an airflow passes through a recently opened membrane closure 72. The airflow exits through a second recently opened membrane closure 73. Throughout the length of the sensor head 12 there are turbulence generating elements to direct flow onto sensing surfaces and create enhanced interactions with said surfaces 74. Adjacent each of the vanes 74 are a sensor appliqué 76 and a return lens 78. Other embodiments include sensors that are not optical, but electrical in their external interface. One or more lasers 80 and modulators 82 are directed at the sensor where the reading is reflected to the return lens 78 via fiber optic lines 86. The multiple lasers 80 and modulators 82 operate at different frequencies for different modes of sensing thereby providing detection of a number of different substances encountered in the air flow path through sensor head 12. The network of fiber optic lines 86 passes the returned laser light that has been transmitted into the air flow path of sensor head 12 and subsequently reflected by sensors appliqués interacting with agents and/or contaminants.

The path of the fiber optics 86 includes one or more detectors 90 and optionally one or more spectral filters 92. Through the operation of filters 92 and detectors 90, sensed reflections that impinge lenses 78 can be analyzed to determine a makeup-up or configuration of any of a number of threatening substances flowing through the sensor head 12.

Figure 4A:
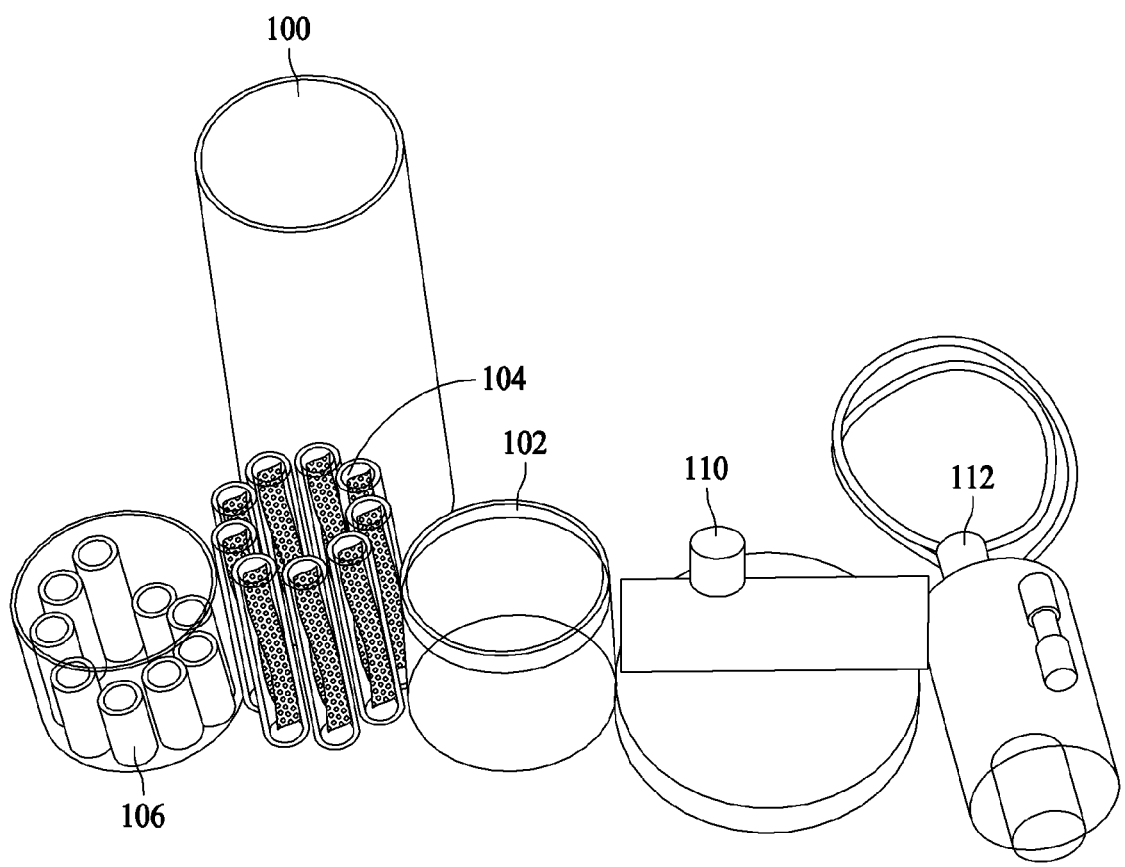
FIG. 4A is an exploded view of the components for one embodiment of a sensor head.
Figure 4B:
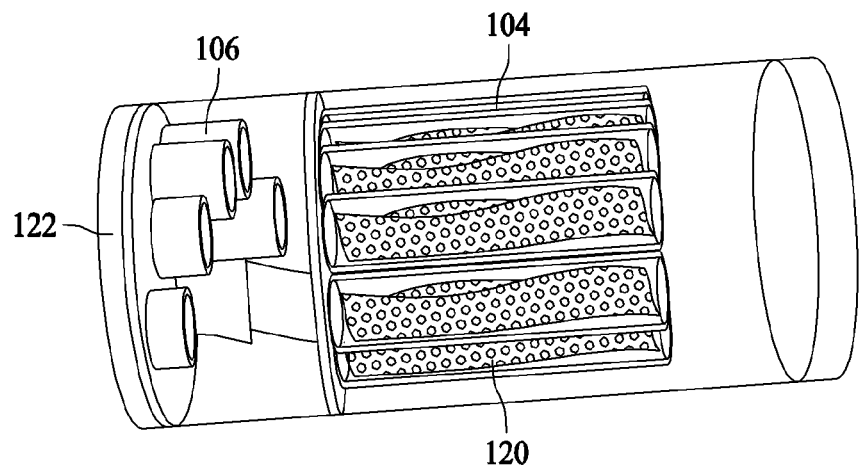
FIG. 4B is an assembled view of the sensor head of FIG. 4A.

FIGS. 4A and 4B are illustrations of the various components of one embodiment for a sensor head 12, where FIG. 4A is an exploded view and FIG. 4B is an assembled view. The illustrated embodiment includes a sensor housing 100, a movable inner housing 102 into which multiple multi-sensor cells 104 are inserted. During operation, a progressive opener 106 works in conjunction with a cutter 110 that operates with the progressive opener 106 and the inner housing 102 to expose one multi-sensor cell 104 to the above described airflow, through a flow through cell 112, for a prescribed period of time. By serially exposing the sensor cells, the sensor head 12 is operational over a longer duration of time. The sensor cells 104 each may include a flow-through membrane 120, that in one embodiment is twisted to enhance flow interaction. The progressive opener 106 and cutter 100 combination is attached to a moving end plate 122, enabling sensing over a period of time. In a specific embodiment, a motor is included within the sensor head 12 to rotate the end plates 122, thereby exposing each sensor cell 104 to the air stream at a prescribed time during the deployment. Other embodiments are envisioned that might include a needle cutter to open a stretched rubber membrane at the proper time.

The characteristics of a parafoil 10 allow for the concentration and mixing of a large volume of air, that is condensed into a column to pass into and through the sensor head 12 for real-time or near real-time analysis. Such a process is herein sometimes referred to as adaptive air column sampling.

Figure 5:
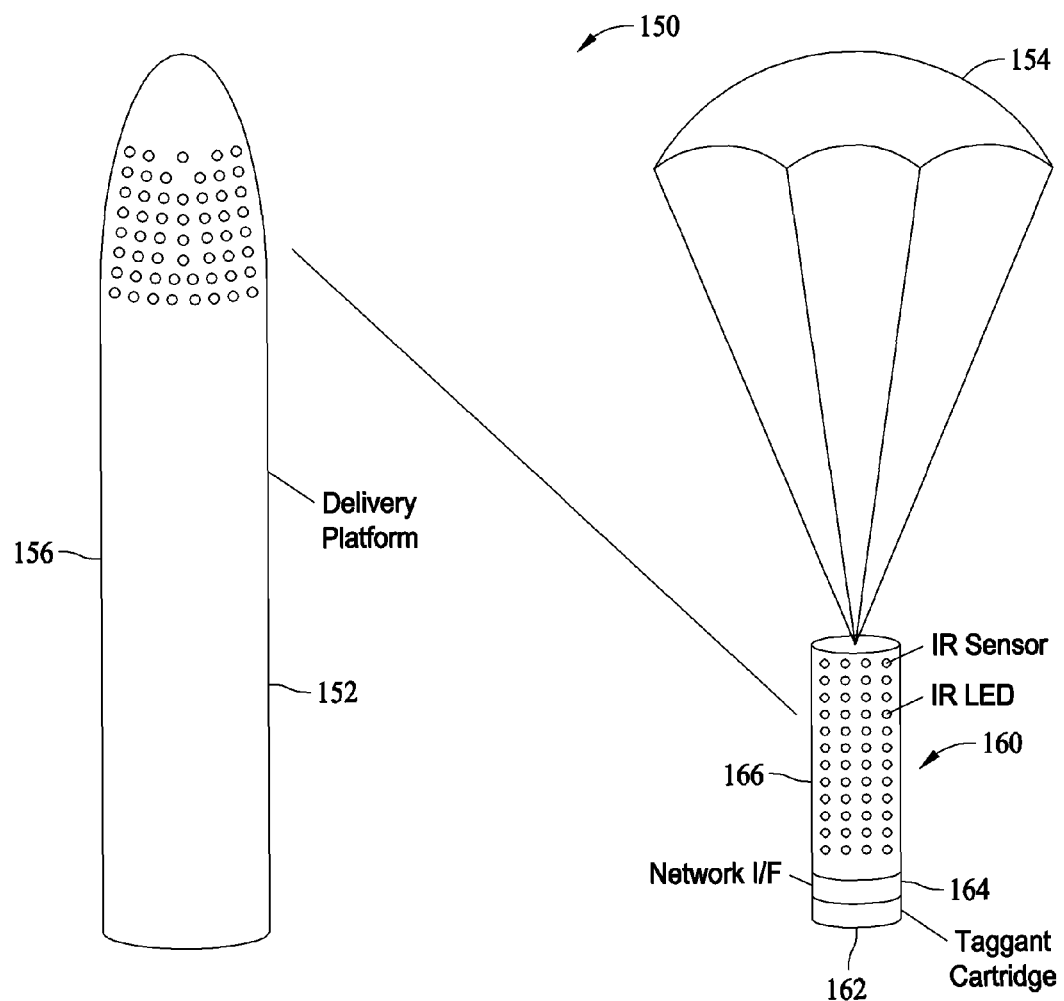
FIG. 5 is an illustration of a sensing device, suspended from a parafoil, configured to characterize airborne contaminants.

FIG. 5 is an illustration of an alternative embodiment for a sensing device 150 configured to characterize airborne contaminants. Specifically, a delivery platform 152 is launched or dropped, for example from a aircraft or other air vehicle. At an appropriate time, a parachute 154 is deployed when a canister 156 of the delivery platform 152 opens. Rather than a parafoil with a flow through center port as in the embodiments described above, a payload 160 is attached to the parachute 154. The payload 160 includes, in the illustrated embodiment, a sensor cartridge 162, a network interface 164, and a bank 166 of illuminators and sensors, for example, infrared LEDs and infrared sensors.

Figure 6:
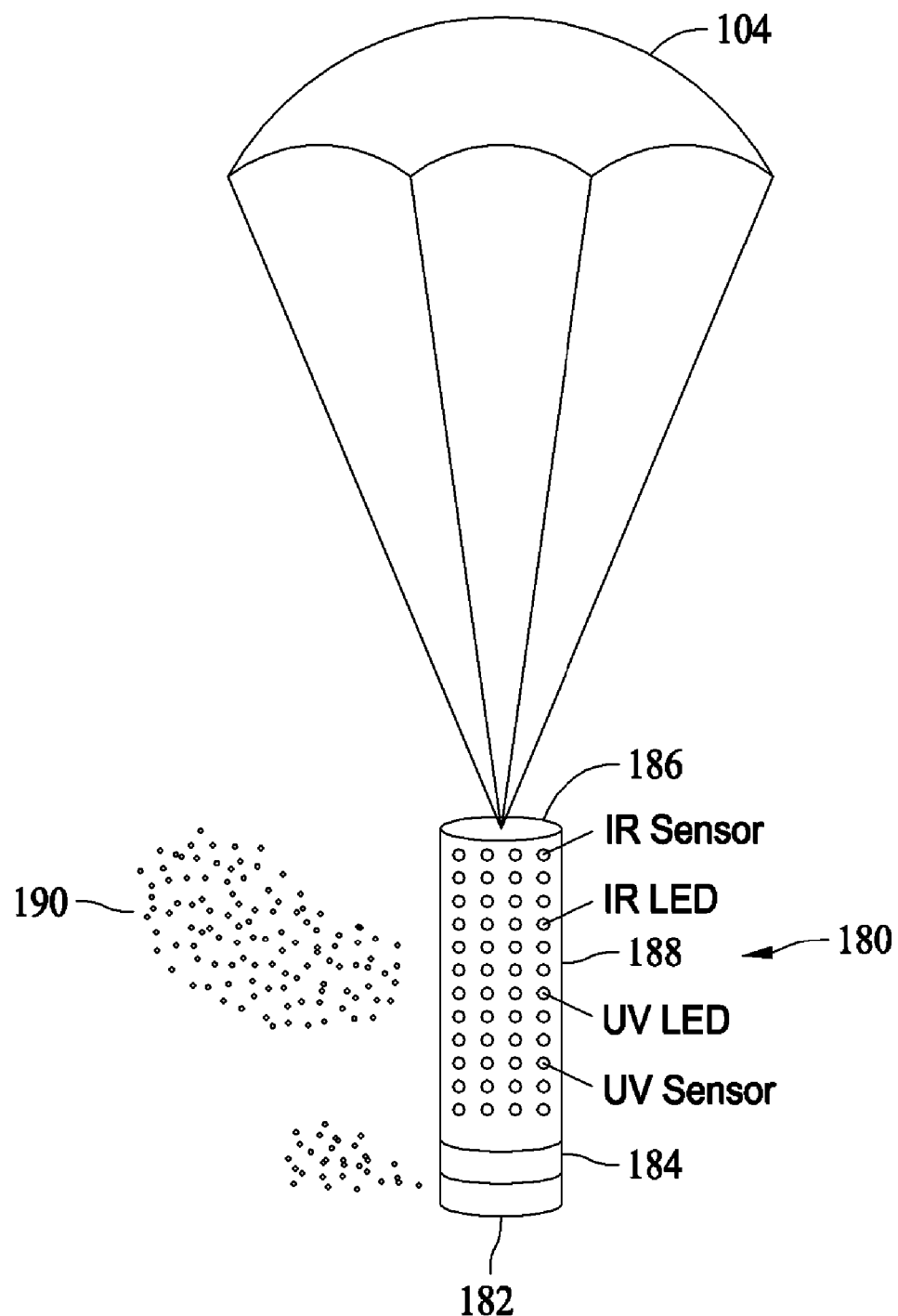
FIG. 6 is an illustration of another sensing device, suspended from a parafoil, configured to characterize airborne contaminants, and illustrating distribution of agent responsive sensors which subsequently flow through the space in proximity to the sensors that read the sensors in addition to the agents.

FIG. 6 illustrates another embodiment of a payload 180. In addition to sensor cartridge 182, a network interface 184, and a bank 186 of infrared LEDs and infrared sensors, payload 180 includes a bank 188 of ultraviolet LEDs and ultraviolet sensors. FIGS. 4-6 also illustrates dispersion of dispersed nano-sensors 190 released from a nano-sensor cartridge 182. In one embodiment, these sensors 190 are spectrally interrogated materials that are treated, or coated, to react when exposed to one or more airborne agents or contaminants.

In other embodiments, such as within sensor head 12, sensors can be attached to a surface using adhesives, applied as appliqués within sensor head 12, or painted on in an appropriately configured paint that causes the surface of the material to be exposed as required for the application. In these embodiments, the sensors can be deployed on the surfaces of the parachute or other funneling device or integrated into the materials from which the parachutes are fabricated. In these configurations, the sensors may be exposed to the agents over a broader surface, and therefore allows a greater sensitivity through integration of a broader sensed surface area.

All of the above described embodiments include sensor target areas, which spatially separate the sensing modalities, and in certain embodiments, spectral separation is leveraged to achieve discrimination of threat agents of various types. This spatial separation enables concurrent sensing and electronic signal processing to provide faster response, greater sensitivity, or higher resistance to false alarm. Proper configuration can achieve all of these goals.

Various sensor types may be utilized. In one embodiment, the target sensors are coated with optically interrogated chemical and/or biological sensor appliqués. Optical illuminators or electronic excitation are utilized in conjunction with optical sensors, for example, one or more of a photodiode, video camera or other appropriate optical/RF sensor, or electronic signal converter to receive the optical, spectral or electrical data which is then processed to indicate the presence of agents and their specific types.

Additionally, the sensing devices may be deployed in a number of ways. For example, the nano-sensors can be distributed (released) into the atmosphere using one delivery platform (the devices of FIGS. 3 and 4), ahead of a second platform such as the device of FIGS. 1 and 2. Once deployed, these nano-sensors pass, for example, through the air stream associated with sensing head 12. The nano-sensor elements are interrogated as they pass each individual section within the sensor head 12.

As those skilled in the art will understand, there are a variety of implementations of the above described airborne sensor and/or sensors, and it easily understandable that these can be mounted in many ways and in many configurations:

In addition to the above described passive parafoil 10 with flow through center port and sensor head 12, other embodiments have been contemplated which are described above. Specifically, sensors embedded or coated onto a passive parafoil, nano-sensors that are distributed into an air column and locally illuminatedor energized for interrogation as it passes into the funnel effect associated with, for example, a flow through port, and flow through chambers acting as ducts or vents to funnel air for concentrated sample management.

The variously described sensor systems incorporate one or more high specificity sensing modalities to characterize the contaminants in a column of air. The sensors utilized afford an adaptive nature that is realized due to the parafoil inflation or extension process. In certain embodiments, to concentrate and assure a broad area is swept in the direction of travel the extension of the parafoil can be fixed or variable in geometry (i.e., the parafoil may only be partially opened if speed dictates lesser area to induce equivalent flows). Passive or active platforms are practical to implement the system, and deployment constraints are based on the characteristic speed and air column size through which the sensors pass. Combinations of mixing elements, reed vanes, and driven fans are utilized in certain applications.

Still other applications incorporate a powered parafoil that is configured with a multiple cell sensor mounted in the air flow.

While the invention has been described in terms of various specific embodiments, those skilled in the art will recognize that the invention can be practiced with modification within the spirit and scope of the claims.

What is claimed is:

1. A method for collecting and sensing a column of air in near real-time to detect one or more agents dispersed within the air column, said method comprising:
   disbursing a plurality of nano-sensors into the air;
   operating a parafoil such that it passes through an area that includes the disbursed nano-sensors:
   passing the column of air through a port in the parafoil, the parafoil configured with a flow-through sensor suite located in the port and operable such that the column of air passes through the sensor suite, at least a portion of the disbursed nano-sensors included in the column of air that passes through the sensor suite;
   operating the sensor suite to test the column of air for the one or more agents; and
   receiving test results from the sensor suite.

2. A method according to claim 1 wherein passing the column of air through a parafoil comprises adaptively directing the column of air to the sensor suite.

3. A method according to claim 1 further comprising transmitting the test results to an external receiver.

4. A method according to claim 1 wherein operating the sensor suite comprises determining if the sensors have interacted with one or more of the agents.

5. A method according to claim 4 wherein determining if the sensors have interacted comprises analyzing spectral data received from the sensors to determine a presence of the one or more agents and a concentration of those agents.

6. A method according to claim 1 wherein passing the column of air through a parafoil comprises utilizing a flow collector to concentrate and mix an increased volume of air to pass through the parafoil.

7. A method according to claim 1 when operating the sensor suite comprises configuring the sensor suite with a plurality of sensor target areas to spatially separate sensing modalities to achieve discrimination for a plurality of different agents.

8. A system for airborne detection of one or more agents dispersed within the atmosphere, said system comprising:
   a parafoil operable to pass through a portion of the atmosphere;
   a sensor suite attached to said parafoil, said sensor suite operable to determine of one or more agents are in the atmosphere portion;
   a plurality of sensors, said sensors disbursable within the atmosphere such that they are detectable by said sensor suite during operation of said parafoil; and
   a processing device configured to receive data from said sensor suite and utilize the received data to discriminate from multiple received signatures to establish the presence or absence of at least one specific agent type.

9. A system according to claim 8 wherein said parafoil comprises a port formed therein, said sensor suite mounted within said port, said parafoil operable such that a column of air passes through said port and said sensor suite.

10. A system according to claim 9 wherein said parafoil is operable to adaptively direct the column of air to said sensor suite.

11. A system according to claim 8 wherein said parafoil comprises one of a parachute, a passive round parafoil, a square chute, a rectangular chute, and a shaped, expandable collector.

12. A system according to claim 8 wherein said sensor suite is configured to detect a presence of at least one of vapors, aerosols, particulates, chemicals, and biological agents.

13. A system according to claim 8 further comprising a receiver, said processing device configured for communication of the data from said sensor suite to said receiver.

14. A system according to claim 8 wherein said plurality of sensors are coated with one or more of an optically interrogated chemical and a biological sensing material.

15. A system according to claim 8 wherein said sensor suite comprises:
   at least one of an optical and an electromagnetic illuminator configured for output onto said sensors interacting with agents passing through said sensor suite; and
   at least one of an optical receiver and an electromagnetic receiver to receive the optical or spectral data reflected from said sensors to determine a presence and concentration of agents within a proximity of said sensor suite.

16. A system according to claim 8 wherein:
   said parafoil comprises a port formed therein, said sensor suite mounted within said port, said parafoil operable such that a column of air passes through said port and said sensor suite; and
   said sensors are distributed into the atmosphere before said parafoil passes through the atmosphere, said sensors interrogated by said sensor suite as they pass through said port as a portion of the column of air.

17. A system according to claim 8 wherein a portion of said parafoil comprises at least one of an embedded material and a coating that comprises one or more of an optically interrogated chemical and a biological sensing material, said sensor suite operable to receive optical or spectral data reflected from said coating to determine a presence and concentration of agents within a proximity of said parafoil.

18. A system according to claim 8 wherein said sensor suite comprises a plurality of sensor target areas placed within said sensor suite to spatially separate sensing modalities to achieve discrimination for a plurality of different agents.

19. A system according to claim 8 wherein said sensor suite comprises at least one of ducts and vents configured to funnel air to concentrate and manage a sample airflow.

20. A system according to claim 8 wherein said sensor suite comprises a plurality of sensor cells, said sensor suite operable to expose individual said sensor cells to the atmosphere portion at prescribed intervals.

* * * * *